United States Patent [19]
Simons

[11] Patent Number: 5,522,387
[45] Date of Patent: Jun. 4, 1996

[54] METHOD TO ASSESS ANESTHESIA

[75] Inventor: Tad D. Simons, Palo Alto, Calif.

[73] Assignee: Hewlett-Packard Company, Palo Alto, Calif.

[21] Appl. No.: 327,163

[22] Filed: Oct. 21, 1994

[51] Int. Cl.$^6$ ........................................................ A61B 5/00
[52] U.S. Cl. ............................................. 128/630; 128/897
[58] Field of Search ..................................... 128/630, 670, 128/671, 700, 897, 898; 364/413.01–413.04

[56] References Cited

U.S. PATENT DOCUMENTS

| | | | |
|---|---|---|---|
| 4,248,241 | 2/1981 | Tacchi | 128/685 |
| 5,195,531 | 3/1993 | Bennett | 128/733 |
| 5,262,944 | 11/1993 | Weisner et al. | 364/413.03 |
| 5,432,698 | 7/1995 | Fujita | 364/413.02 |
| 5,438,983 | 9/1995 | Falcone | 128/630 |

*Primary Examiner*—Lee S. Cohen
*Assistant Examiner*—Samuel Gilbert

[57] ABSTRACT

A patient's general state of anesthesia is displayed as a Cartesian plot of two vital signs: heart rate and blood pressure, in a window on a monitor. The heart rate is plotted on the x-axis while blood pressure is plotted on the y-axis. An anesthetist selects minimum and maximum values for each vital sign which are appropriate for the patient. These limits denote a desired zone which is indicated on the display. As the heart rate and the blood pressure are monitored, the general state is shown as an indicator on the plot as a multi-variable function of the two vital signs. When the indicator is within the desired zone, the two vital signs are in an acceptable range. When the indicator is outside of the desired zone, a visual or audible alarm indicates potential patient distress.

16 Claims, 1 Drawing Sheet

5,522,387

METHOD TO ASSESS ANESTHESIA

FIELD OF THE INVENTION

The present invention relates to vital sign monitors and, more specifically to displaying a patient's vital signs during an operation. The invention illustrates a state of the patient that depends upon multiple vital signs in a single window on a display.

BACKGROUND OF THE INVENTION

Patients are placed in a state of general anesthesia for their comfort during surgery. General anesthesia is a reversible state where a patient achieves three conditions: adequate analgesia (insensitivity to pain), a degree of paralysis, and a degree of amnesia. Because these conditions vary from patient to patient, continual observation is necessary to assure a proper state of anesthesia. Furthermore, for each phase of a surgery, the depth of these three conditions varies.

Anesthesia is induced by administering pharmacological agents which include volatile inhalation agents, analgesics, narcotics, and muscle relaxants. Individual patients exhibit a wide range in their physiological response to these drugs, so that anesthesiologists cannot rely on knowledge of the dosage alone to predict the desired state of anesthesia. Furthermore, the effects of these agents vary in time as the patient's body absorbs and metabolizes the drugs. Mixtures of agents can have anesthetic effects which are different than the effects of each agent alone. As mentioned earlier, the conditions of anesthesia may change during each phase of surgery, including initial induction, maintenance during surgery, and recovery. During these times, the anesthesiologist must titrate the patient to the desired state by varying the mixture and dose of the anesthetic agents. Anesthesiologists rely on a variety of observations to assess the adequacy of the state of anesthesia. These observations include examination of the eye and skin, reflex responses to stimuli, change (or cessation) of breathing, and physiological vital signs.

Two commonly observed vital signs are heart rate (HR) and blood pressure (BP). Physiological monitors measure these signs (continually or intermittently) and display their values as single numbers. These values are often displayed on separate instruments. Patients under stress, i.e. under painful stimuli, display normal physiological reactions, such as stimulations of sympathetic and para-sympathetic nervous systems. Notably, they can experience cardiovascular stimulation which causes increases in HR and BP. Thus, anesthesiologists watch HR and BP to determine if they have provided adequate anesthesia. Falling HR and BP can mean too much anesthesia or narcotic, and also indicate generally compromised cardiovascular function.

If the state of anesthesia is not deep enough, even unconscious patients will experience pain and show increases in their HR and BP. Inadequately anesthetized patients can also move involuntarily, which is undesirable during surgery. A state of anesthesia that is too deep may compromise patient organ systems and complicate recovery from the pharmacological agents. Some anesthetic agents have increased toxicity when given in large doses. Therefore, anesthesiologists try to maintain anesthesia that is adequate, but not excessive. This is especially important in patients who are very weak or ill.

Currently, anesthesiologists note the initial "resting" state of the HR and BP before inducing anesthesia. During anesthesia, they observe changes in HR and BP from numbers on displays of two physiological monitors to help judge the state of the patient. Because vital sign displays are read in an area often crowded with other displays, performing the mental calculations about the significance of any physiological changes is subject to some error.

What is needed is a method of display which indicates the amount and degree of change in HR and BP in a single, unambiguous, and recognizable format.

SUMMARY OF THE INVENTION

A patient's general state of anesthesia is displayed as a Cartesian plot of two vital signs: heart rate and blood pressure, in a window on a display. The heart rate is plotted on the x-axis while blood pressure is plotted on the y-axis. An anesthetist selects minimum and maximum values for each vital sign which are appropriate for the patient. These values denote a desired zone which is indicated on the display. As the heart rate and the blood pressure are monitored, the general state is shown as an indicator on the plot as a multi-variable function of the two vital signs. When the indicator is within the desired zone, the patient is comfortable. When the indicator moves outside of the desired zone, a visual or audible alarm indicates potential patient distress.

DETAILED DESCRIPTION OF THE PREFERRED EMBODIMENTS

Figure 1:
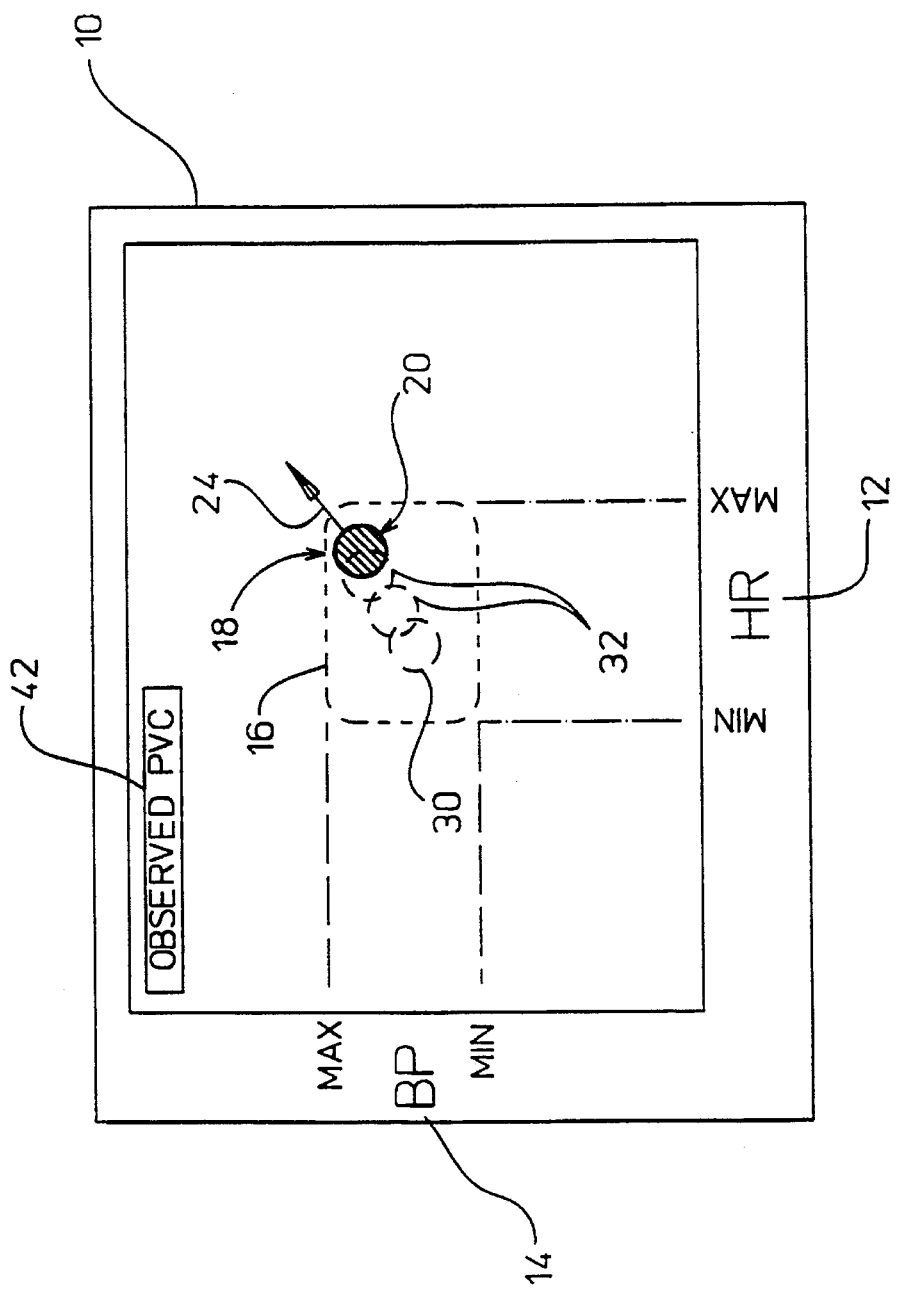
FIG. 1 illustrates a display format of two vital signs as a multivariable function.

A patient's general state of anesthesia can be displayed as a Cartesian plot of two vital signs: heart rate and blood pressure, in a window on a display. The heart rate is plotted on the x-axis while blood pressure is plotted on the y-axis. An anesthesiologist selects a minimum and a maximum value for each vital sign which are specific for the patient. These values denote a desired zone which is indicated on the display. As the heart rate and the blood pressure are monitored, the general state is shown as an indicator on the plot as a multi-variable function of the two vital signs. When the indicator is within the desired zone, the two vital signs are in an acceptable range. When the indicator is outside of the desired zone, the patient is in potential distress.

FIG. 1 illustrates a display format 10 of two vital signs of a patient as a multi-variable function. The two vital signs 12, 14, such as heart rate and blood pressure, are displayed on a Cartesian graph. The x-axis is labelled as the heart rate and the y-axis is labelled as the blood pressure. An anesthesiologist selects an optional minimum and a maximum value for each vital sign, appropriate for the patient. These optional minimum and maximum values define a desired zone 16, which is indicated on the display. An indicator 18 indicates the general state of the patient. The indicator may include a numerical display 20 which shows the current value of either of the two vital signs. As long as the indicator 18 remains within the desired zone 16, the patient has vital signs in an acceptable range. If the indicator 18 drifts out of the desired zone 16, the patient may need additional anesthesia, or the anesthesiologist may need to check other conditions, such as the status of patient ventilation. The anesthesiologist can titrate the patient into this desired state by observing the indicator (and other patient signs) and administering (or reducing dosages of) pharmacological agents.

An additional arrow 24 can be added to the indicator to indicate the direction of change in the parameters. This feature is useful to judge the type of change incurring in the patient, such as the effect of administering additional anesthesia, of patient response to stimuli. The direction of the arrow indicates the current direction of change for the patient's general state. The length of the arrow can vary dynamically to indicate the rate of change in the general state of the patient. The direction and size of the arrow are useful guides for the anesthesiologist when the patient is being titrated to the desired state.

The indicator may also have different colors. Each color indicates the patient's general state. For example, while the indicator remains in the desired zone, the indicator is green. On an edge of the desired zone, the indicator changes to yellow. Out of the desired zone, the indicator becomes red. A blinking indicator strengthens the visual illustration of undesired states. It may be desirable to leave a residual indicator 30 of the initial state on the window (presumably in the desired zone) to show how far the patient has drifted from the initial state during the surgery. It may be desirable also to leave residual indicators 32, representing other previous general states of the patient, to show a path between the current general state and some previous general state. As a substitute for (or in the absence of) a tone signal, the indicator could have an associated tone which indicates the heartbeat.

If other physiological observations of heart rate and blood pressure are relevant, such as ectopic heart beats or reduced S-T segments in the electrocardiogram, then these physiological observations may appear in a small window 42 on the same display.

A suitable location for the display is in a portion of the greater display of a conventional monitor of vital signs, which is always observed by the clinician. The display is best suited as a window on the greater display of an "anesthesiology workstation". Such a workstation would manage all the data for the anesthesiologist in the operating room such as monitoring information, record keeping, drug management, ventilation data, and data from the anesthesia machine. As part of a greater display, alarms generated by the multi-variable plot could function in an integrated alarm system.

From the foregoing, it will be appreciated that the present invention provides a convenient method for determining the general state of a patient, particularly during surgery.

I claim:

1. A method for displaying a general state of anesthesia of a patient as a multi-variable function comprising the steps of:

determining a first and a second range, wherein the first range is associated with a first vital sign and second range is associated with a second vital sign;

monitoring the first and the second vital signs;

determining a general state of the patient from the monitored first and second vital signs; and displaying an indicator corresponding to the general state of anesthesia of the patient as a multi-variable plot having the first vital sign as a variable on a first variable on a first axis and the second vital sign as a variable on a second axis.

2. A method for displaying a general state of anesthesia, as defined in claim 1, wherein the first vital sign is heart rate and the second vital sign is blood pressure.

3. A method for displaying a general state of anesthesia, as defined in claim 1, wherein:

the step of determining a first and a second range further includes the steps of:

determining first minimum and maximum values associated with the first vital sign, and determining second minimum and maximum values associated with the second vital sign, wherein the first minimum and maximum values and the second minimum and maximum values define a desired zone unique to the patient; and the step of displaying an indicator further includes indicating patient distress when the general state of anesthesia is not within the desired zone.

4. A method for displaying a general state of anesthesia, as defined in claim 3, wherein the step of displaying an indicator further comprises the step of displaying the desired zone.

5. A method for displaying a general state of anesthesia, as defined in claim 3, further comprising the step of activating an alarm when the indicator is outside the desired zone.

6. A method for displaying a general state of anesthesia, as defined in claim 5, wherein the indicator has a color and activating an alarm changes the color of the indicator.

7. A method for displaying a general state of anesthesia, as defined in claim 5, wherein the step of activating an alarm changes an audible tone.

8. A method for displaying a general state of anesthesia, as defined in claim 5, wherein the step of activating an alarm intermittently blinks the indicator.

9. A method for displaying a general state of anesthesia, as defined in claim 1, wherein the step of displaying an indicator further comprises the step of displaying a change in direction of the general state of anesthesia of the patient.

10. A method for displaying a general state of anesthesia, as defined in claim 9, wherein the step of displaying an indicator further includes the step of indicating a rate of change in the general state of anesthesia of the patient.

11. A method for displaying a general state of anesthesia, as defined in claim 10, wherein the step of indicating a rate of change is indicated dimensionally.

12. A method for displaying a general state of anesthesia, as defined in claim 1, wherein the Step of displaying an indicator further comprises the step of displaying an initial general state of anesthesia of the patient.

13. A method for displaying a general state of anesthesia, as defined in claim 1, wherein the step of displaying an indicator further comprises the step of displaying previous general of anesthesia states of the patient.

14. A method for displaying a general state of anesthesia, as defined in claim 1, wherein the step of displaying an indicator further comprises the step of symbolically displaying the general state of anesthesia of the patient within the indicator.

15. A method for displaying a general state of anesthesia, as defined in claim 1, wherein the step of displaying an indicator further comprises the step of displaying a physiological observation that is independent of the multi-variable plot.

16. A method for displaying a general state of anesthesia, as defined in claim 1, further comprising displaying the first and the second ranges as a zone on the multi-variable plot.

* * * * *